United States Patent [19]
Li

[11] Patent Number: 5,428,855
[45] Date of Patent: Jul. 4, 1995

[54] ROTATABLE TOOTHBRUSH

[76] Inventor: Rui-Long Li, 58, Ma Yuan West St., Taichung, Taiwan

[21] Appl. No.: 272,843

[22] Filed: Jul. 11, 1994

[51] Int. Cl.⁶ ............................................. A46B 13/02
[52] U.S. Cl. ................................................... 15/23
[58] Field of Search .............................. 15/23, 24, 25

[56] References Cited

U.S. PATENT DOCUMENTS

| | | | |
|---|---|---|---|
| 2,275,247 | 3/1942 | Cavanagh | 15/23 |
| 2,310,626 | 2/1943 | Gold | 15/23 |
| 2,533,107 | 12/1950 | Grover | 15/23 |
| 2,583,886 | 1/1952 | Schlegel | 15/23 |
| 3,258,802 | 7/1966 | Rodriguez | 15/23 |
| 3,800,350 | 4/1974 | Francolino | 15/23 |
| 3,927,434 | 12/1975 | Burgess | 15/23 |
| 4,181,997 | 1/1980 | O'Rourke | 15/24 |
| 5,044,035 | 9/1991 | Barradas | 15/23 |

FOREIGN PATENT DOCUMENTS

| | | | |
|---|---|---|---|
| 0488971 | 6/1992 | European Pat. Off. | 15/23 |
| 955499 | 1/1950 | France | 15/24 |
| 3306969 | 5/1984 | Germany | 15/23 |
| 15408 | 12/1933 | United Kingdom | 15/25 |
| 1012110 | 12/1965 | United Kingdom | 15/23 |
| 8303956 | 11/1983 | WIPO | 15/23 |

*Primary Examiner*—David A. Scherbel
*Assistant Examiner*—Randall E. Chin

[57] ABSTRACT

A toothbrush includes a handle and a head secured to each other. A spindle and a shaft are rotatably supported in the handle. Two rods for carrying bristles are rotatably supported in the head and fixed to the spindle and the shaft. Two gears are secured on the spindle and the shaft and meshed with each other. A motor is coupled to the spindle for rotating the spindle and the shaft. The rods are rotated reversely by the motor via the gears. A cover is pivotally coupled to the head for opening the head in order to replace the bristles.

1 Claim, 3 Drawing Sheets

ROTATABLE TOOTHBRUSH

BACKGROUND OF THE INVENTION

1. Field of the Invention

The present invention relates to a toothbrush, and more particularly to a rotatable toothbrush.

2. Description of the Prior Art

A typical toothbrush is shown in FIG. 1 and comprises a shank and a bristle head, the bristle head is operated manually. A typical rotatable toothbrush is shown in FIG. 2 and comprises a handle having a motor disposed therein, and a bristle head coupled to the motor such that the bristle head may be rotated by the motor. However, the bristle head may be rotated in one direction only. In addition, the bristle head may not be changed, the whole rotatable toothbrush should be discarded when the bristle head is worn out.

The present invention has arisen to mitigate and/or obviate the afore-described disadvantages of the conventional toothbrushes.

SUMMARY OF THE INVENTION

The primary objective of the present invention is to provide a rotatable toothbrush in which the bristle head may be replaced.

In accordance with one aspect of the invention, there is provided a toothbrush comprising a handle and a head secured to each other, a motor disposed in the handle, a spindle rotatably supported in the handle and coupled to the motor and driven by the motor, a rod for carrying bristle being rotatably supported in the head and secured to the spindle and rotated in concert with the spindle, and the head including a cover pivotally coupled thereto for opening the head in order to replace the rod.

A shaft is further rotatably supported in the handle and arranged in parallel to the spindle, another rod for carrying bristle is rotatably supported in the head and secured to the shaft and rotated in concert with the shaft, two gears are secured on the spindle and the shaft respectively and meshed with each other, such that the rods are rotated reversely by the motor. The head includes a frame having two ends, two panels are disposed on the ends of the frame, a notched ring is engaged in each of the panels for engaging with rod so as to rotatably support the rod.

Further objectives and advantages of the present invention will become apparent from a careful reading of a detailed description provided hereinbelow, with appropriate reference to accompanying drawings.

DETAILED DESCRIPTION OF THE PREFERRED EMBODIMENT

Figure 1:
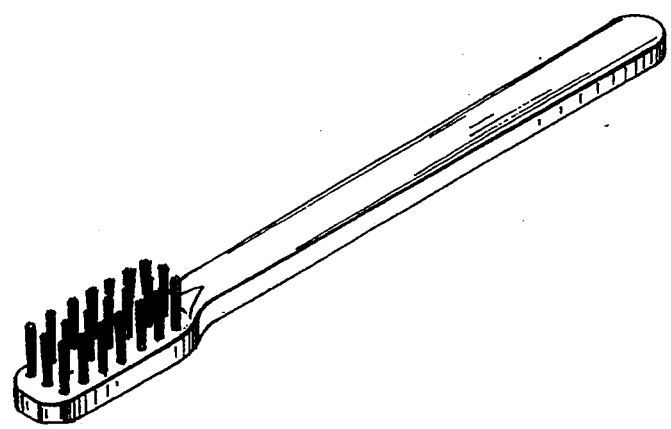
FIGS. 1 and 2 are perspective views illustrating two typical toothbrushes.
Figure 2:
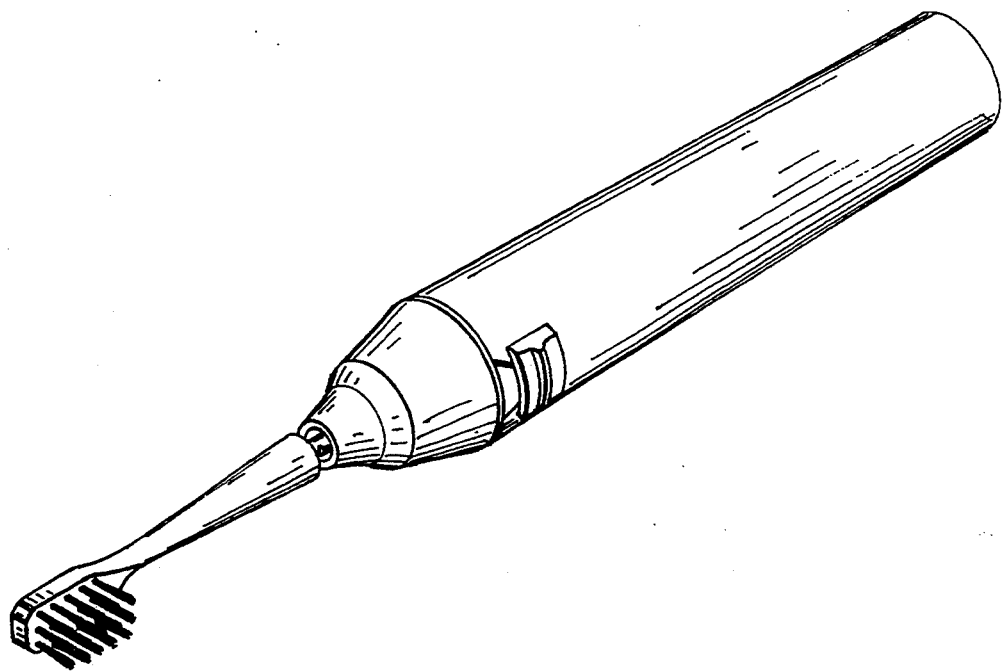
Figure 3:
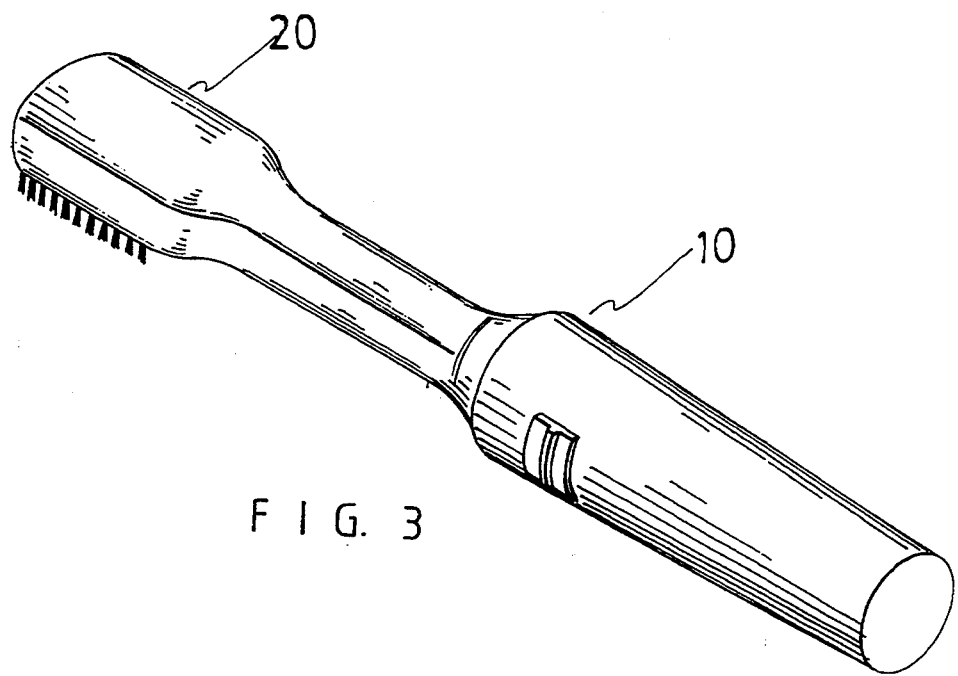
FIG. 3 is a perspective view of a toothbrush in accordance with the present invention.
Figure 4:
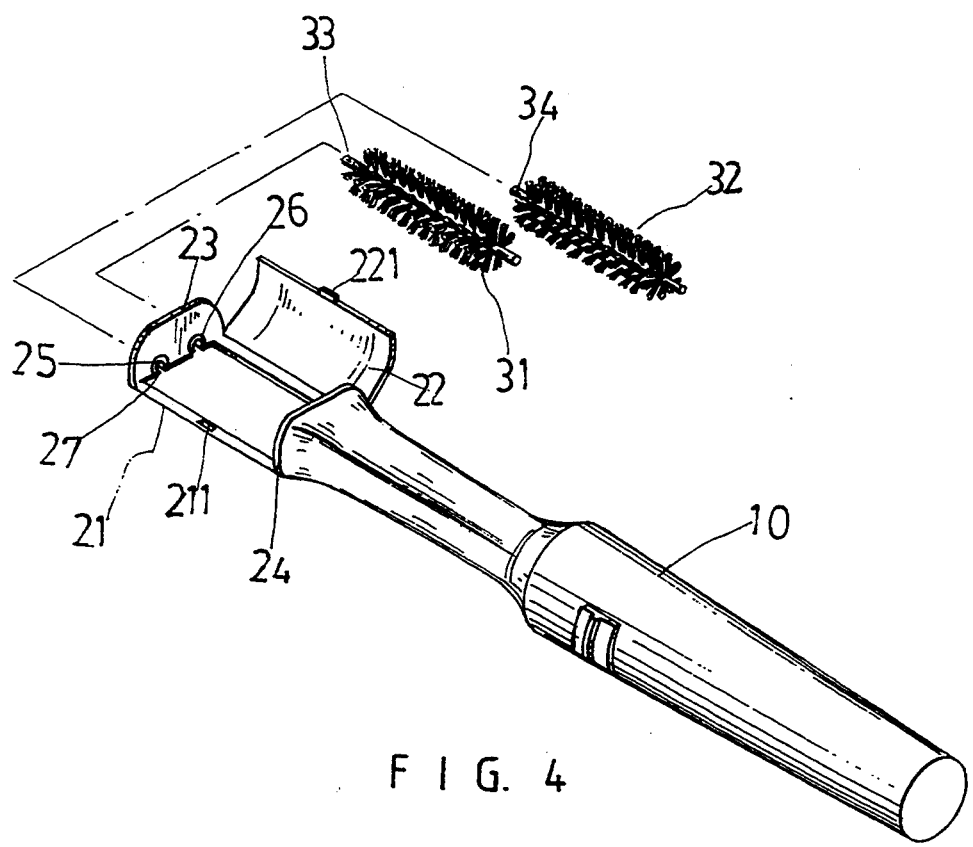
FIG. 4 is a partial exploded view of the toothbrush.
Figure 5:
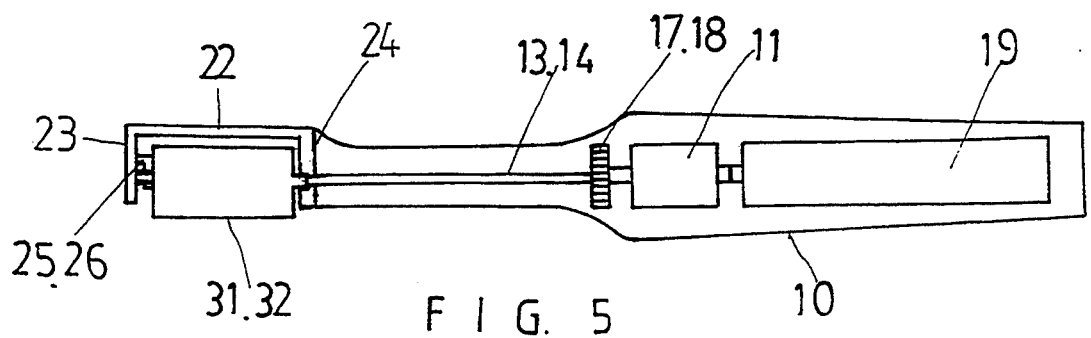
FIG. 5 is a schematic view illustrating the interior of the toothbrush.
Figure 6:
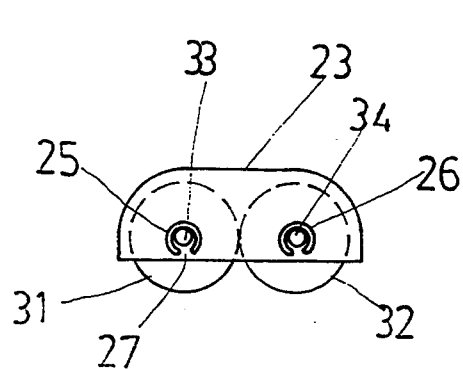
FIGS. 6 and 7 are schematic views illustrating the configuration of the bristle head.

Referring to the drawings, and initially to FIGS. 3 to 5, a rotatable toothbrush in accordance with the present invention comprises a handle 10 and a head 20 secured with each other. The handle 10 includes a motor 11 and a battery 19 disposed therein. A spindle 14 is coupled to the motor 11 and rotated by the motor. A shaft 13 is rotatably supported in the handle 10, arranged in parallel to the spindle 14, and extended toward the head 20. A gear 18 is secured on the spindle 14 for engaging with another gear 17 which is fixed on the shaft 13, such that the spindle 14 and the shaft 13 may be rotated by the motor 10 simultaneously. Two rods 33, 34 are secured to the spindle 14 and the shaft 13, respectively and have bristles 31, 32 secured thereon.

Figure 7:
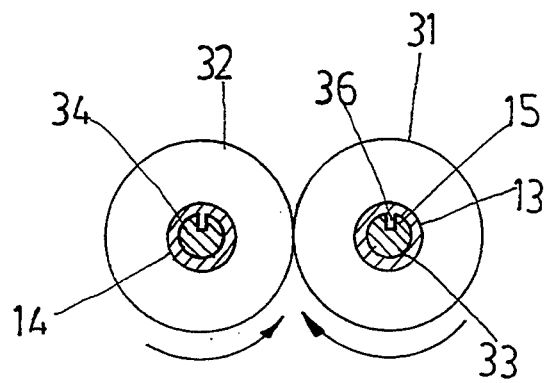

The head 20 includes a frame 21 having two ends and having a groove 211 formed in the middle portion thereof. A cover 22 is pivotally coupled to the frame 21 and includes a catch 221 for engaging with the groove 211 so as to secure the cover 22 to the frame 21. A pair of panels 23, 24 are disposed on the ends of the frame 21 respectively. Each of the panels 23, 24 includes two openings 27 formed therein, two notched rings 25, 26 are secured in the openings 27, respectively. The end portions of the rods 33, 34 may be engaged in the rings 25, 26 via the notches thereof and the rods 33, 34 may be rotatably supported in place by the rings 25, 26. As shown in FIG. 7, the rods 33, 34 have one end engaged in the spindle 14 and the shaft 13, respectively, each of the rods 33, 34 includes a notch 15 formed therein for engaging with the key 36 of the spindle 14 and the shaft 13 such that the rods 33, 34 are rotated in concert with the shaft 13 and the spindle 14, respectively.

Figure 8:
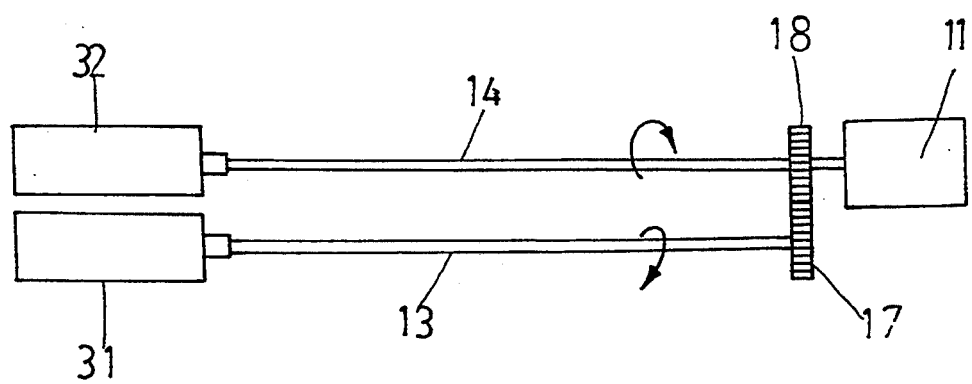
FIG. 8 is a schematic view illustrating the operation of the toothbrush.

In operation, as shown in FIGS. 7 and 8, the bristles 31, 32 may be rotated reversely by the motor 11. In addition, the bristles 31, 32 may be easily replaced when worn out.

Although this invention has been described with a certain degree of particularity, it is to be understood that the present disclosure has been made by way of example only and that numerous changes in the detailed construction and the combination and arrangement of parts may be resorted to without departing from the spirit and scope of the invention as hereinafter claimed.

I claim:

1. A toothbrush comprising a handle and a head secured to each other, a motor disposed in said handle, a spindle rotatably supported in said handle and coupled to said motor and driven by said motor, a shaft rotatably supported in said handle and arranged in parallel to said spindle, a first rod for carrying bristles being rotatably supported in said head and secured to said spindle and rotated in concert with said spindle, a second rod for carrying bristles being rotatably supported in said head and secured to said shaft and rotated in concert with said shaft, a first gear secured on said spindle and a second gear secured on said shaft and engaged with said first gear such that said first rod and said second rod are rotated in opposite directions with respect to each other by said motor via said gears, said head including a frame having two ends, two panels disposed on said ends of said frame, notched ring means engaged in said panels for engaging with said rods, and said head including a cover pivotally coupled thereto or opening said head in order to replace said rods.

\* \* \* \* \*